United States Patent [19]

Nelson

[11] 4,128,577

[45] Dec. 5, 1978

[54] 15-METHYL- AND 16-PHENOXY-PGF$_2\alpha$, AMIDES

[75] Inventor: Norman A. Nelson, Galesburg, Mich.

[73] Assignee: The Upjohn Company, Kalamazoo, Mich.

[21] Appl. No.: 859,639

[22] Filed: Dec. 12, 1977

Related U.S. Application Data

[63] Continuation-in-part of Ser. No. 719,055, Aug. 30, 1976, Pat. No. 4,073,808, which is a continuation-in-part of Ser. No. 645,276, Dec. 29, 1975, abandoned.

[51] Int. Cl.$^2$ ............................................. C07C 177/00
[52] U.S. Cl. .............................. 260/559 B; 260/561 B
[58] Field of Search ......................... 260/561 B, 559 B

[56] References Cited

U.S. PATENT DOCUMENTS

| 3,987,085 | 10/1976 | Yankee | 260/240 R |
| 3,987,087 | 10/1976 | Bundy | 260/240 R |

*Primary Examiner*—Paul J. Killos
*Attorney, Agent, or Firm*—Robert A. Armitage

[57] ABSTRACT

The present invention relates to certain prostaglandin-type amides which are useful as intermediates in preparing corresponding 2-decarboxy-2-aminomethyl prostaglandin analogs. In addition to their use as chemical intermediates, these compounds are further useful for inducing prostaglandin-type physiological responses, especially being regulators of fertility.

2 Claims, No Drawings

15-METHYL- AND 16-PHENOXY-PGF$_2\alpha$, AMIDES

CROSS REFERENCE TO RELATED APPLICATIONS

This application is a continuation-in-part of co-pending application Ser. No. 719,055, filed Aug. 30, 1976, now U.S. Pat. No. 4,073,808, which is a continuation-in-part of co-pending application Ser. No. 645,276, filed Dec. 29, 1975, now abandoned.

SUMMARY OF THE INVENTION

The present invention relates to novel amides of certain PGF$\alpha$-type compounds. In particular, the present invention relates to the novel amides disclosed in U.S. Ser. No. 719,055, filed Aug. 30, 1976, now U.S. Pat. No. 4,073,808, issued Feb. 14, 1978, the disclosure of which is incorporated here by reference.

In particular, U.S. Pat. No. 4,073,808 describes the use of certain PGF$\alpha$-type amides as intermediates for preparing 2-decarboxy-2-aminomethyl-PGF$\alpha$-type compounds. With respect to U.S. Pat. No. 4,073,808, particular reference is made to Chart G, especially Formulas CIII and CIV therein.

Moreover, the examples in U.S. Pat. No. 4,073,808 provide examples of the preparation of amides according to Formula CIII of Chart D therein. Accordingly there are described 15-Methyl-PGF$_2\alpha$, amide in Examples 1 and 12;
PGF$_1\alpha$, amide in Example 3; and
16-Phenoxy-17,18,19,20-tetranor-PGF$_2\alpha$, amide, following Example 12.

As indicated in the text associated with Chart G in U.S. Pat. No. 4,073,808, the method for preparing the 2-decarboxy-2-aminomethyl-PGF$\alpha$-type compound of Fomula CIV is by aluminum hydride reduction of the Formula CIII PGF$\alpha$-type amide. Thus, with respect to each of the 2-decarboxy-2-aminomethyl-PGF$\alpha$-type compounds according to Formula CIV of Chart G which are described in Tables A–I of U.S. Pat. No. 4,073,808, there are further described and prepared according to the procedure of Chart G the corresponding PGF$\alpha$-type amides according to Formula CIII. Moreover, for each of the 2-decarboxy-2-aminomethyl-PGF$\alpha$-type compounds of Tables A–I, there is described in the text of U.S. Pat. No. 4,073,808 preceding these Tables a description of 2-decarboxy-2-aminomethyl-11-deoxy-PGF$\alpha$-type compounds corresponding to each of the 2-decarboxy-2-aminomethyl-PGF$\alpha$-type compounds in the Tables. Likewise, the method of Chart G of U.S. Pat. No. 4,073,808 provides 11-deoxy-PGF$\alpha$-type amides corresponding to each of these 2-decarboxy-2-aminomethyl-11-deoxy-PGF$\alpha$-type compounds.

Among the PGF$\alpha$- or 11-deoxy-PGF$\alpha$-type amides thusly described, certain of these compounds represent novel chemical entities comprising one aspect of the present invention. Moreover, for these novel PGF$\alpha$-type amides, another aspect of the present invention comprises the surprising and unexpected discovery that these novel PGF$\alpha$-type amides are useful for the same pharmacological purposes and in the same manner as the corresponding acids, esters, or C-1 amines (i.e., 2-decarboxy-2-aminomethyl-PGF$\alpha$-type compounds).

This pharmacological utility for these novel PGF$\alpha$-type amides is especially evidenced in their use as agents for the control or regulation of the reproductive cycle of mammalian species. In particular, these novel PGF$\alpha$-type amides are useful as labor inducers, abortifacients, or menstrual regulators in the manner described in U.S. Pat. No. 4,073,808 for the corresponding 2-decarboxy-2-aminomethyl-PGF$\alpha$-type compounds.

While these novel PGF$\alpha$-type amides are formulated in the same manner as described in U.S. Pat. No. 4,073,808 for the corresponding 2-decarboxy-2-aminomethyl compounds, one particularly important and useful route of administration is vaginally, employing suppositories containing an amount of a novel PGF$\alpha$-type amide such that one or more of such suppositories delivers an amount of drug effective to induce the desired effect on the reproductive system.

In the formulation of these suppositories containing the novel PGF$\alpha$-type amide, conventional techniques are employed. Thus, the effective amount of the novel PGF$\alpha$-type amide is combined with a conventional suppository base. While any number of a wide variety of suppository bases are commercially acceptable, one specific requirement for such a base is that it exhibit a M.P. at 37–39° C. A typical suppository base useful for this purpose would, for example, be one composed of 90% triglycerides of 10 to 20 carbon atoms and 10% of mono- and diglycerides of 10 to 20 carbon atoms.

Such a conventional suppository would, for example, in humans weight about 2.2 g and contain about 0.1–50 mg of novel PGF$_2\alpha$-type amide. For example, when such a suppository containing 15-methyl-PGF$_2\alpha$, amide is prepared, about 3–7 mg of the novel amide is present in the 2.2 g suppository.

The surprising and unexpected utility of the novel PGF$\alpha$ amides is evidenced in the following example.

EXAMPLE A

15-Methyl-PGF$_2\alpha$, amide (5 mg) is dissolved in a conventional suppository base composed of C$_{10}$–C$_{20}$ triglycerides (90%) and C$_{10}$–C$_{20}$ mono- and diglycerides (10%). On day 101 of pregnancy, a female Rhesus monkey is treated vaginally with the suppository thusly prepared. Uterine activity is monitored with an intraamniotic open-ended catheter. An increase in uterine activity is noted about 15 min after suppository insertion, being manifest by a slight increase in contraction amplitude and basal uterine tone. About 45 min after insertion, the amplitude of contractions is doubled and the uterine tone is significantly increased. Very rhythmatic strong uterine contractions are noted about 75 min after insertion and persist for the duration of recording (about 4 hr after treatment). Pregnancy is terminated between 24 and 48 hrs after insertion. No side effects are observed during the entire course of treatment.

Amides (i.e., —CONH$_2$ derivatives) of certain prostaglandins and analogs thereof are known in the art. See especially U.S. Pat. Nos. 3,853,951; 3,884,942; 3,903,299; 3,880,885; and 3,953,470. See further foreign patents and published applications, as follows: French Published Applications Nos. 2,239,458 (Derwent CPI No. 32921W) and 2,315,915 (Derwent CPI No. 20752X) and British Published Specification No. 1,356,581 (Derwent CPI No. 26079T abstracting German Offenlegungsschrift No. 2,150,361).

I claim:
1. 15-Methyl-PGF$_2\alpha$, amide.
2. 16-Phenoxy-17,18,19,20-tetranor-PGF$_2\alpha$, amide.

* * * * *